United States Patent [19]
Pavcnik et al.

[11] Patent Number: 5,350,398
[45] Date of Patent: Sep. 27, 1994

[54] SELF-EXPANDING FILTER FOR PERCUTANEOUS INSERTION

[76] Inventors: Dusan Pavcnik, Klanec #15, Nova Gorica, Slovenija, 65000, Yugoslavia; Sidney Wallace, 3324 Pittsburg, Houston, Tex. 77005; Kenneth C. Wright, 1802 Haver, Houston, Tex. 77006

[21] Appl. No.: 68,594

[22] Filed: May 28, 1993

Related U.S. Application Data

[63] Continuation of Ser. No. 699,190, May 13, 1991, abandoned.

[51] Int. Cl.$^5$ .............................................. A61M 29/00
[52] U.S. Cl. .................................................. 606/200
[58] Field of Search ............... 606/200, 198, 191, 195; 623/1, 12

[56] References Cited

U.S. PATENT DOCUMENTS

| | | |
|---|---|---|
| 3,540,431 | 11/1970 | Mobin-Uddin . |
| 3,952,747 | 4/1976 | Kimmell, Jr. . |
| 4,425,908 | 1/1984 | Simon . |
| 4,494,531 | 1/1985 | Gianturco . |
| 4,580,568 | 4/1986 | Gianturco . |
| 4,619,246 | 10/1986 | Molgaard-Nielsen et al. . |
| 4,643,184 | 2/1987 | Mobin-Uddin . |
| 4,688,553 | 8/1987 | Metals . |
| 4,727,873 | 3/1988 | Mobin-Uddin . |
| 4,781,177 | 11/1988 | Lebigot . |
| 4,793,348 | 12/1988 | Palmaz . |
| 4,817,600 | 4/1989 | Herms et al. . |
| 4,832,055 | 5/1989 | Palestrant . |
| 4,969,891 | 11/1990 | Gewertz . |
| 5,108,419 | 4/1992 | Reger et al. ................. 606/200 |

OTHER PUBLICATIONS

Barry T. Uchida, James S. Putnam, and Josef Rosch, *Modifications of Gianturco Expandable Wire Stents*, A. J. R. 150: 1185–1187, American Roentgen Ray Society (1988).

Shigeru Furui, M.D., Satoshi Sawada, M.D., Toshiyuki Irie, M.D., Kohzoh Makita, M.D., Teiyu Yamauchi, M.D., Syoichi Kusano, M.D., Kenji Ibukuro, M.D., Hironobu Nakamura, M.D., Eiichi Takenaka, M.D., PhD., *Hepatic Inferior Vena Cave Obstruction: Treatment of Two Types with Gianturco Expandable Metallic Stents*, Radiology 176: 665–670 (1990).

Chusilp Charnsangavej, M.D., Sidney Wallace, M.D., Kenneth C. Wright, Ph.D. C. Humberto Carrasco, M.D., Cesare Gianturco, M.D., *Endovascular Stent for Use in Aortic Dissection: An in Vitro Experiment*, Radiology 1577: 323–324 (1985).

Josef Rosch, M.D., Jane E. Bedell, M.D., James Putnam, M.D., Ruza Antonovic, M.D., and Barry Uchida, B. S., *Gianturco Expandable Wire Stents in the Treatment of Superior Vena Cava Syndrome Recurring After Maximum–Tolerance Radiation*, Cancer 60: 1243–1246 (1987).

*Stenosis of the Vena Cava: Preliminary Assessment of Treatment with Expandable Metallic Stents*, Radiology 161: 295–298, (1986).

B. G. Fallone, PhD., S. Wallace, M.D., and C. Gianturco, M.D., *Elastic Characteristics of the Self-Expanding Metallic Stents*, Invest. Radiology 23: 370–376 (1988).

Tetsuya Yoshioka, Kenneth C. Wright, Sidney Wallace, David D. Lawrence, Jr., Cesare Gianturco, *Self-Expanding Endovascular Graft: An Experimental Study in Dogs*, A.J.R. 151: 673–676, American Roentgen Ray Society (1988).

*Self-expanding Stainless Steel Biliary Stents*, Radiology 170: 979–983 (1989).

*Gianturco Expandable Metallic Biliary Stents: Results of a European Clinical Trial*, Radiology 172: 321–326 (1989).

(List continued on next page.)

*Primary Examiner*—Michael H. Thaler

[57] ABSTRACT

A flexible vena cava filter comprises a flexible stent having a plurality of flexible wire segments attached across the ends of the stent. The filter is resiliently compressible for percutaneous insertion into a fluid passageway and expands against the passageway upon placement therein. The filter includes different levels of filtration.

11 Claims, 2 Drawing Sheets

OTHER PUBLICATIONS

Kenneth C. Wright PhD., *Percutaneous Transcatheter Stent Placement*, Radiology 176: 620–621 (1990).

*Recurrent Benign Biliary Strictures: Management with Self-Expanding Metallic Stents*, Radiology 175: 661–665 (1990).

P. J. M. George, J. D. Irving, B. S. Mantell, R. M. Rudd, *Covered Expandable Metal Stent for Recurrent Tracheal Obstruction*, Lancet 335: 582–584 (1990).

*Tracheobronchial Tree: Expandable Metallic Stents Used in Experimental and Clinical Applications*, Radiology 158: 309–312 (1986).

Kenneth C. Wright, PhD., Sidney Wallace, M.D., Chusilp Charnsangavej, M.D., C. Humberto Carrasco, M.D., Cesare Gianturco, *Percutaneous Endovascular Stents: An Experimental Evaluation*, Radiology 156: 69–72 (1985). 69–72 (1985).

*Self-Expanding Metallic Stents for Samll Vessels: An Experimental Evaluation*, Radiology 162: 469–472 (1987).

Sidney Wallace, M.D., Cesare Gianturco, M.D., et al., *Self-Expanding Metallic Stents: Preliminary Evaluation in an Atherosclerotic Model*, Radiology 163: 739–742 (1987).

*Superior Vena Cava Syndrome Associated with Massive Thrombosis: Treatment with Expandable Wire Stents*, Radiology 167: 727–728 (1988).

Kenneth C. Wright, PhD., et al., *Percutaneously Placed Endovascular Grafts for Aortic Aneurysms: Feasibility Study*, Radiology 170: 1033–1037 (1989).

Klaus Rauber, Christian Franke, and Wigbert S. Rau, *Self-Expanding Stainless Steel Endotracheal Stents: An Animal Study*, Rontgenabteilung Innere Medizen des Zentrums der Radiologie der Kliniken der Justis-Liebig-Unerversitat, Springer Verlag New York Inc., (1989).

M. Darcy and W. R. Castaneda-Zuniga, *Percutaneous Vena Cava Filtering*, Angiographic Management of Vascular Obstruction 706–716.

Gary S. Dorfman, M.D., *Percutaneous Inferior Vena Caval Filters*, Radiology 174: 987–992 (1990).

M. J. Wallace, K. Ogawa, K. Wright, C. H. Carrasco, Wm. Richli, C. Charnsangavej, *Inferior Vena Caval Stent Filter*, A.J.R. 147: 1247–1250 (1986).

David D. Lawrence, Jr., M.D. et al., *Percutaneous Endovascular Graft: Experimental Evaluation*, Radiology 163: 357–360 (1987).

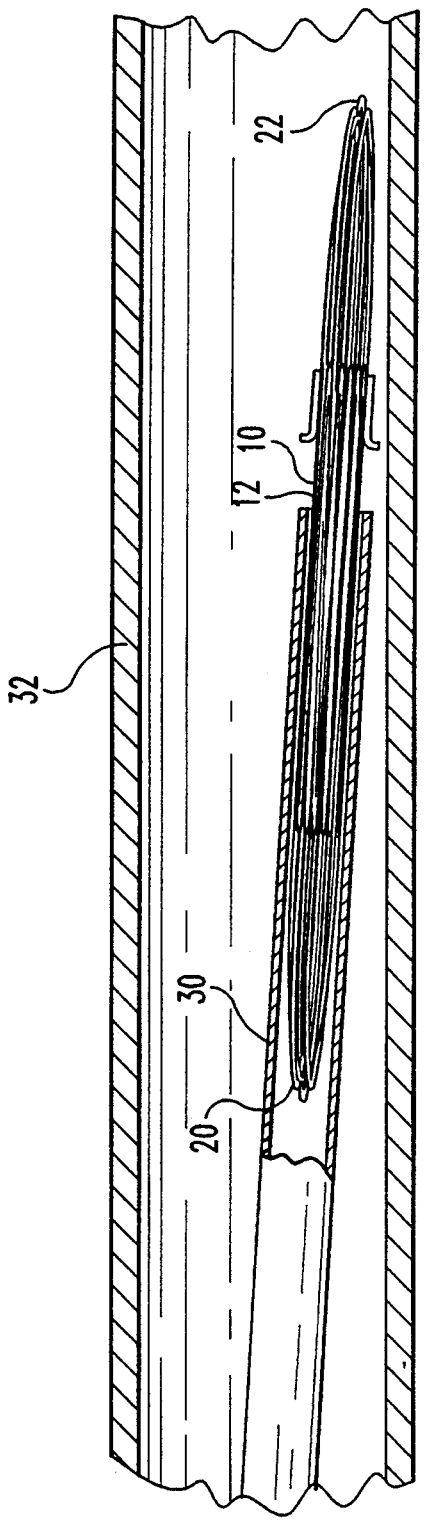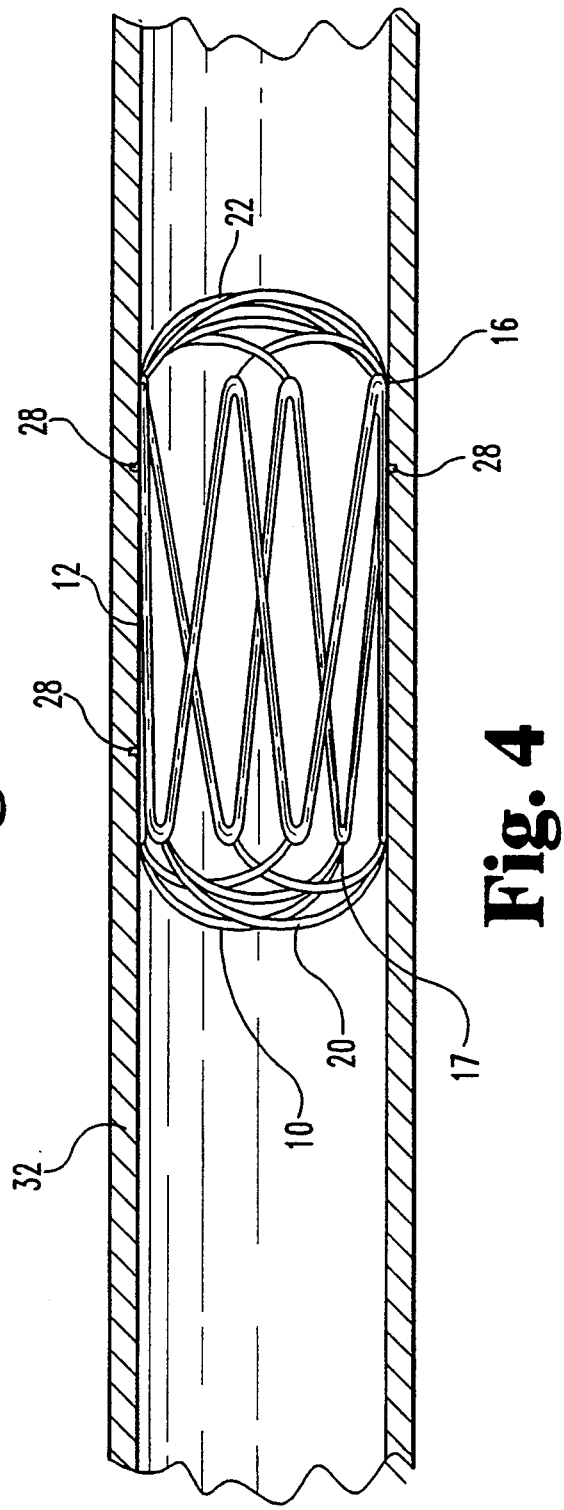

SELF-EXPANDING FILTER FOR PERCUTANEOUS INSERTION

This application is a continuation of application Ser. No. 07/699,190, filed May 13, 1991, now abandoned.

BACKGROUND OF THE INVENTION

This invention relates in general to filters and more specifically to flexible filters for percutaneous insertion and placement within a fluid passageway of a living body.

Pulmonary embolism is a disease occurring at a frequency of over 600,000 symptomatic cases per year in the United States. Pulmonary embolism is the sudden obstruction of a blood vessel by blood emboli, the emboli typically formed in the veins of the pelvis and lower extremities of a living body. Because migration of the blood emboli to the pulmonary artery can interrupt the oxygenization process in the lungs, the disease has a high mortality rate with over 200,000 deaths each year in the United States. Vena cava filters, therefore, have been developed as one method for preventing pulmonary embolism.

Historically, vena cava filters have been implanted surgically requiring ligation of the inferior vena cava. Although initially effective against pulmonary embolism, caval ligation carries a very high operative mortality, up to 50% in some cases. This high mortality rate stimulated development of devices that could be placed within the caval lumen which do not require general anesthesia and surgery. One device by Mobin-Uddin, U.S. Pat. No. 3,540,431, describes a filter comprising a skeletal body of struts expandable into a generally domed shaped configuration. Besides requiring a relatively large sized sheath for percutaneous insertion, this filter design can be susceptible to migration and to caval thrombosis. Other domed shaped filters include Gewertz, U.S. Pat. No. 4,969,891; Lebigot, U.S. Pat. No. 4,781,177; Metals, U.S. Pat. No. 4,688,553; and others by Mobin-Uddin, U.S. Pat. Nos. 4,643,184 and 4,727,873.

Other filters including a head with a plurality of legs extending therefrom are described by Herms et al., U.S. Pat. No. 4,817,600; Palmax, U.S. Pat. No. 4,793,348; and Kimmell, Jr., U.S. Pat. No. 3,952,747. These types of filters typically suffer problems including filter tilt, misplacement and migration.

In an attempt to overcome these problems, still other filters have been developed including Gianturco, U.S. Pat. No. 4,494,531. The Gianturco filter comprises a number of strands of shaped memory wire interconnected and tangled together to form a curly wire mesh, or "bird's nest". Another filter by Molgaard-Nielsen et al., U.S. Pat. No. 4,619,246, describes a collapsible filter basket comprising a plurality of resilient wires interconnected at their respective ends. Finally, Palestrant, U.S. Pat. No. 4,832,055, describes a mechanically locking blood clot filter, and Simon, U.S. Pat. No. 4,425,908, describes a blood clot filter comprising a material being pliable in its low temperature condition and being resiliently deformable and rigid in its high temperature condition.

While the above filters can be percutaneously inserted thus precluding surgery and its inherent mortality risks, there still exists a need for an improved percutaneously insertable filter providing greater ease of insertion, broader range of application and increased effectiveness. Such a filter should be insertable using a simple single step procedure employing transcatheter techniques. Such a device should also be collapsible into a small shape to pass through a small catheter system. Also desired is a device which is self-expanding, self-centering and includes multiple planes of filtration.

SUMMARY OF THE INVENTION

A flexible filter for percutaneous insertion and placement within a fluid passageway of a living body according to one embodiment of the present invention comprises a flexible stent and a first plurality of flexible wire segments attached across the stent. The filter is resiliently compressible into a first insertion form for percutaneous insertion into the passageway, wherein the stent and the wire segments resiliently bend to store energy therein. The filter is resiliently expandable into a larger operational form within the passageway by the release of the energy stored in the stent and the wire segments, wherein the stent resiliently unbends to support open the passageway and the wire segments resiliently unbend to form a first filter element across the passageway.

One object of the present invention is to provide an improved apparatus for a percutaneously installed filter.

Another object of the present invention is to provide a percutaneously installed filter which is easily inserted, the filter collapsible for percutaneous insertion.

Another object of the present invention is to provide a filter which is self-expanding, self-centering and has multiple planes of filtration.

Related objects and advantages of the present invention will become apparent from the following description.

BRIEF DESCRIPTION OF THE DRAWINGS

FIG. 3 is a side cross-sectional view of the flexible filter of FIG. 1 collapsed within a distal end of a sheath and partially deployed within a passageway.

FIG. 4 is a side cross-sectional view of the flexible filter of FIG. 1 fully deployed within the passageway.

DESCRIPTION OF THE PREFERRED EMBODIMENT

Figure 1:
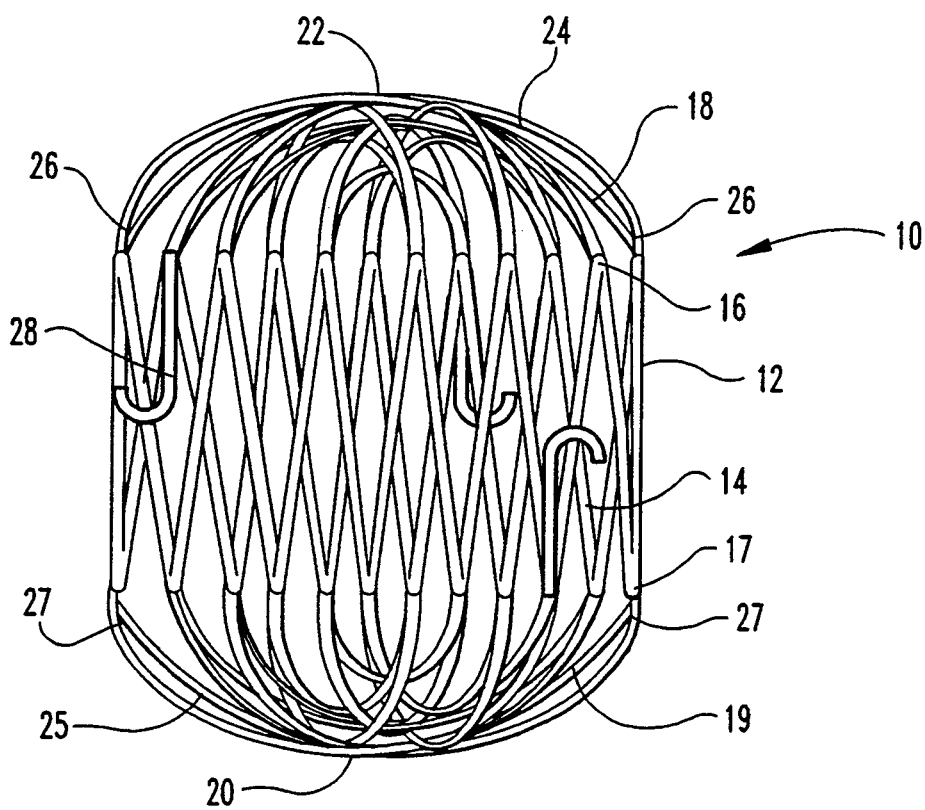
FIG. 1 is a side elevational view of a flexible filter according to one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a flexible filter 10 is shown in its expanded form. Filter 10 includes a stent 12 comprising a wire formed into a closed zig-zag configuration including an endless series of straight wire sections 14 joined by a plurality of bends 16, defining a cranial end, and bends 17, defining a caudal end, to form the stent. Preferably, stent 12 is a Gianturco self-expanding stent as described in U.S. Pat. No. 4,580,568, which description is incorporated herein by reference.

Attached to the ends of stent 12 are a plurality of flexible wire segments 18 and 19, which define a portion of a hemispherical surface at each end of the stent. Wire segments 19 loop across the caudal end of stent 12 to form a caudal filter element 20. Wire segments 18 loop across the cranial end of stent 12 to form a cranial filter element 22. Also contemplated are wire segments which attach across and between the ends of the filter; for example, across the middle of the filter. In the preferred embodiment, wire segments 18 are formed from a single stainless steel flexible safety wire 24 approximately 30 cm. in length. The safety wire 24 has a plurality of bends 26 defining the wire segments 18 therebetween. Similarly, wire segments 19 are formed from safety wire 25 having a plurality of bends 27 defining the wire segments 19 therebetween.

Also contemplated are a plurality of individual wires or wire segments looped across the ends of stent 12; however, single wire attached at a plurality of points provides an added safety factor should an attachment point fail. For example, an individual wire/wire segment upon failing at both attachment points at each end thereof would release from the filter to migrate with collateral damage possibly resulting. A single wire with a plurality of bends defining wire segments therebetween can fail at two attachment points and still remain attached to the stent.

Figure 2:
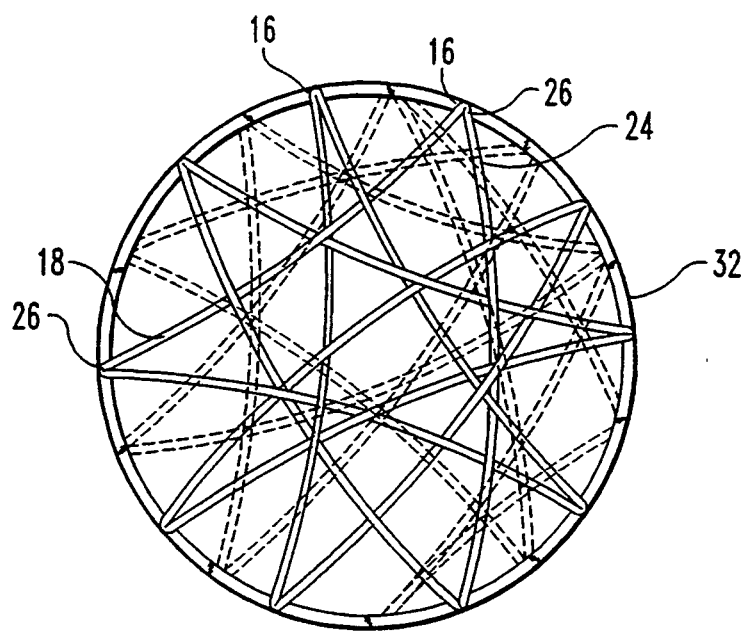
FIG. 2 is a top plan view of the flexible filter depicted in FIG. 1 inserted in a fluid passageway.

Referring now to FIG. 2, wire 24 is shown attached to the cranial end of stent 12 at bends 26. Bends 26 of wire 24 attach to bends 16 of stent 12. Wire segments 18 are formed between the attachment points of wire 24 to stent 12 and overlap each other to form the cranial filter element 22. Wire 25 similarly attaches to the caudal end of stent 12 at bends 27, with bends 27 of wire 25 attaching to bends 17 of stent 12. Wire segments 19 are formed between the attachment points of wire 25 to stent 12 and overlap each other to form the caudal filter element 20. Wire segments 18 and 19, corresponding to filter elements 22 and 20 respectively, are attached to the ends of the stent employing a pattern. Preferably the segments include common chordal lengths which result in a crossing pattern and yield common openings defining a filtration size.

Different filtration levels or sizes can be provided by changing the number of wire segments looped across the two ends of the stent. For example, the caudal filter element might filter blood emboli having a size greater than 6 mm., while the cranial filter element might filter smaller blood emboli having sizes between 3 and 6 mm. Changes in filtration sizes are easily accomplished in the preferred embodiment by changing the number of bends in wires 24 and 25 and the length of wire segments between bends.

Filter 10 also preferably includes a number of hooks or barbs 28 attached to stent 12. Barbs 28 assist in fixing filter 10 within a fluid passageway to prevent migration. The barbs can be opposed or oppositely facing so that the filter can be deployed from either end. Additionally, stent 12 and filter elements 20 and 22 operate to press filter 10 against the fluid passageway to assist fixing filter 10 therein, :due to residual energy remaining within stent 12 and filter elements 20 and 22 after expansion. Tissue ingrowth of the passageway into stent 12 can fix filter 10 therein as well. Wires 24 and 25, defining filter elements 22 and 20 respectively, and barbs 28 are soldered onto stent 12; however, welding and other attachment means known in the art can be employed as well.

Referring now to FIG. 3, filter 10 is shown partially contained within a sheath or catheter 30 to permit percutaneous entry into the fluid passageway. In the preferred embodiment, catheter 30 is a 12-French catheter. Stent 12 is resiliently compressible into catheter 30 prior to percutaneous insertion. Upon insertion and deployment from catheter 30, stent 12 automatically expands against the passageway 32 as shown in FIG. 4. As depicted in FIG. 3, filter 10 radially compresses within catheter 30 while filter elements 20 and 22 longitudinally compress within the length of catheter 30. Energy in the form of stress is stored in stent 12 and filter elements 20 and 22 when compressed. Stent 12 primarily stores energy in its bends, while filter elements 20 and 22 store energy in the deflected wire segments. Catheter 30 is depicted in FIG. 3 with filter 10 partially deployed within fluid passageway 32. To deploy filter 10, a pusher catheter (not shown) slidably engaged within catheter 30 holds filter 10 in place within passageway 32 while the catheter 30 is withdrawn. Upon release from catheter 30, filter 10 automatically expands against passageway 32 due to the stored energy within stent 12 and filter elements 20 and 22.

Referring now to FIG. 4, filter 10 is depicted fully deployed within passageway 32. Barbs 28 engage within passageway 32 to assist in fixing filter 10 in place.

The diameter of filter 10 can be varied to accommodate various passageway diameters by changing the number of bends 16 and 17 contained in stent 12. One range of filter designs includes filters ranging from 2.4 to 3.4 cm. in diameter, wherein the filter is 2 centimeters long and is constructed from 0.012 inch diameter stainless steel wire. This size range for filter 10 allows for placement in most inferior vena cavas.

Filter 10 can be placed either from the femoral or jugular vein approach. Because the cranial and caudal networks of wire segments forming filter elements 20 and 22 are flexible, filter insertion is easily accomplished even when the veins are tortuous. In one specific example of filter 10 having filter elements 20 and 22 with different filtration sizes for placement in dogs, a 12-French introducer sheath was inserted into the inferior vena cava via the femoral vein. Under fluoroscopic monitoring, the sheath was advanced to a point just below the orifice of renal veins. Filter 10 was advanced through the introducer sheath using a pusher catheter. When the filter reached the end of the sheath, the pusher catheter held the filter in place while the sheath was withdrawn. The filter opened as it exited the introducer. A large number of radiopaque emboli of different sizes were injected into the femoral vein to evaluate filter efficiency. The emboli which passed the first filtration level were caught at the second level.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A filter for placement within a fluid passageway of a living body, comprising:
 a self-expanding stent having an endless series of wire sections joined by bends into a closed zig-zag configuration that is compressible to a reduced diameter but being resiliently self-expanding from said reduced diameter to an enlarged diameter;

wherein said stent has a cranial end and caudal end defined by said bends;

a plurality of first wire segments attached across one end of said stent, each of said first wire segments having a first end and a second end, said first end being attached to a bend and said second end being attached to another different bend;

wherein portions of said first wire segments overlap each other;

a plurality of second wire segments attached across the other end of said stent, each of said second wire segments having a first end and a second end, said first end being attached to a bend and said second end being attached to another different bend;

wherein portions of said second wire segments overlap each other;

wherein said first wire segments define a first plurality of openings having a large filtration size; and said second wire segments define a second plurality of openings having a relatively smaller filtration size.

2. The filter of claim 1 wherein said first wire segments are made form a single strand of wire, and said first wire segments are attached to one another by a series of wire bends.

3. The filter of claim 1 further comprising at least one barb attached to said stent for securing said filter to said passageway upon placement therein.

4. The filter of claim 1 wherein said bends at each end of said stent are consecutively arranged around a central axis; and each of said first wire segments is attached between non-consecutive bends.

5. A filter for placement within a fluid passageway of a living body, comprising a self-expanding stent having an endless series of wire sections joined by bends into a closed zig-zag configuration that is compressible to a reduced diameter but being resiliently self-expanding from said reduced diameter to an enlarged diameter;

wherein said stent has a cranial end and a caudal end defined by said bends, which are consecutively arranged around a central axis;

a plurality of first wire segments attached across one end of said stent, each of said first wire segments having a first end and a second end, said first end being attached to a bend and said second end being attached to another different bend;

wherein each of said first wire segments is attached between non-consecutive bends;

a plurality of second wire segments attached across the other end of said stent, each of said second wire segments having a first end and a second end, said first end being attached to a bend and said second end being attached to another different bend; and wherein said first wire segments define a first plurality of openings having a large filtration size; and said second wire segments define a second plurality of openings having a relatively smaller filtration size.

6. The filter of claim 5 wherein said first wire segments are made from a single strand of wire, and said first wire segments are attached to one another by a series of wire bends.

7. The filter of claim 5 further comprising at least one barb attached to said stent for securing said filter to said passageway upon placement therein.

8. A filter for placement within a fluid passageway of living body, comprising:

a self-expanding stent having an endless series of wire sections joined by bends into a closed zig-zag configuration that is compressible to a reduced diameter but being resiliently self-expanding from said reduced diameter to an enlarged diameter;

wherein said stent has a cranial end and a caudal end defined by said bends;

a plurality of first wire segments attached across one end of said stent, each of said first wire segments having a first end and a second end, said first end being attached to a bend and said second end being attached to another different bend;

wherein said first wire segments define a portion of a hemispherical surface;

a plurality of second wire segments attached across the other end of said stent, each of said second wire segments having a first end and a second end, said first end being attached to a bend and said second end being attached to another different bend; and wherein said first wire segments define a first plurality of openings having a large filtration size; and said second wire segments define a second plurality of openings having a relatively smaller filtration size.

9. The filter of claim 8 wherein said first wire segments are made from a single strand of wire, and said first wire segments are attached to one another by a series of wire bends.

10. The filter of claim 8 further comprising at least one barb attached to said stent for securing said filter to said passageway upon placement therein.

11. The filter of claim 8 wherein said bends at each end of said stent are consecutively arranged around a central axis; and each of said first wire segments is attached between non-consecutive bends.

* * * * *